United States Patent [19]

Geiger et al.

[11] Patent Number: 5,175,306

[45] Date of Patent: Dec. 29, 1992

[54] PROCESS FOR THE RESOLUTION OF RACEMATES OF OPTICALLY ACTIVE BICYCLIC IMINO-α-CARBOXYLIC ESTERS

[75] Inventors: Rolf Geiger, Frankfurt am Main; Volker Teetz, Hofheim am Taunus; Dietrich Langner, Frankfurt am Main, all of Fed. Rep. of Germany

[73] Assignee: Hoechst Aktiengesellschaft, Frankfurt am Main, Fed. Rep. of Germany

[21] Appl. No.: 562,402

[22] Filed: Aug. 3, 1990

Related U.S. Application Data

[60] Continuation of Ser. No. 300,908, Jan. 24, 1989, abandoned, which is a division of Ser. No. 23,277, Mar. 9, 1987, abandoned, which is a division of Ser. No. 575,401, Jan. 30, 1984, abandoned.

[30] Foreign Application Priority Data

Jan. 31, 1983 [DE] Fed. Rep. of Germany ....... 3303112

[51] Int. Cl.⁵ .................. C07D 209/52; C07D 209/12
[52] U.S. Cl. .................................... 548/452; 548/453
[58] Field of Search ............................... 548/452, 453

[56] References Cited

U.S. PATENT DOCUMENTS

| | | | |
|---|---|---|---|
| 4,374,847 | 2/1983 | Gruenfeld | 514/415 |
| 4,508,729 | 4/1985 | Vincent et al. | 514/419 |
| 4,525,301 | 6/1985 | Henning et al. | 548/411 |
| 4,558,064 | 12/1985 | Teetz et al. | 514/409 |
| 4,558,065 | 12/1985 | Urbach et al. | 514/412 |
| 4,562,202 | 12/1985 | Urbach et al. | 514/223 |
| 4,587,258 | 5/1986 | Gold et al. | 514/412 |
| 4,591,598 | 5/1986 | Urbach et al. | 514/412 |
| 4,614,805 | 9/1986 | Urbach et al. | 548/427 |
| 4,620,012 | 10/1986 | Henning et al. | 548/411 |
| 4,659,838 | 4/1987 | Lerch | 548/452 |
| 4,668,797 | 5/1987 | Urbach et al. | 548/452 |
| 4,684,662 | 8/1987 | Henning et al. | 548/452 |
| 4,691,022 | 9/1987 | Henning et al. | 548/408 |
| 4,714,708 | 12/1987 | Urbach et al. | 514/412 |
| 4,727,160 | 2/1988 | Teetz et al. | 548/452 |
| 4,808,573 | 2/1989 | Gold et al. | 514/19 |
| 4,818,749 | 4/1989 | Gold et al. | 514/19 |
| 4,831,157 | 5/1989 | Gold et al. | 548/452 |

FOREIGN PATENT DOCUMENTS

| | | |
|---|---|---|
| 0012845 | 7/1980 | European Pat. Off. |
| 0018549 | 11/1980 | European Pat. Off. |
| 0037231 A2 | 10/1981 | European Pat. Off. |
| 0046953 | 3/1982 | European Pat. Off. |
| 0049658 | 4/1982 | European Pat. Off. |
| 0050850 A1 | 5/1982 | European Pat. Off. |
| 0079022 | 5/1983 | European Pat. Off. |
| 0090362 | 10/1983 | European Pat. Off. |
| 0012401 | 3/1984 | European Pat. Off. |
| 3226768 | 5/1983 | Fed. Rep. of Germany |
| 3322530 | 1/1985 | Fed. Rep. of Germany |
| 812859 | 3/1982 | Finland |
| 813283 | 4/1982 | Finland |
| 813422 | 5/1982 | Finland |
| 2491469 | 4/1982 | France |
| 57-77672 | 5/1982 | Japan |
| 57-112359 | 7/1982 | Japan |
| 57-91974 | 8/1982 | Japan |
| 198535 | 9/1984 | New Zealand |
| 198702 | 8/1985 | New Zealand |
| 81/5988 | 8/1982 | South Africa |
| 832229 | 12/1983 | South Africa |
| 87/2230 | 9/1987 | South Africa |
| 2086390 | 5/1981 | United Kingdom |
| 2095682 | 4/1985 | United Kingdom |

OTHER PUBLICATIONS

Leonard et al., J. Am. Chem. Soc., 77, 439 (1955).
Leonard et al., J. Am. Chem. Soc., 78, 3457 (1956).
Leonard et al., J. Am. Chem. Soc., 78, 3463 (1956).
Leonard et al., J. Am. Chem. Soc., 81, 5627 (1959).
Koelsch et al., J. Org. Chem., 26, 1104 (1961).
Griot et al., Helv. Chim. Acta, 42, 121 (1959).
Bonnett et al., J. Chem. Soc., 2087 (1959).
Battersby et al., J. Chem. Soc., 4333 (1958).
Rosenblatt et al., The Chemical of Functional Groups. Supplement F: The Chemistry of Amino, Nitroso and Nitro Compounds And Their Derivatives, Part II, S. Patai, ed., Wiley & Sons: New York, 1982, pp. 1100–1104.

(List continued on next page.)

Primary Examiner—David B. Springer
Attorney, Agent, or Firm—Finnegan, Henderson, Farabow, Garrett and Dunner

[57] ABSTRACT

The invention relates to a process for resolving racemic mixtures of bicyclic imino-α-carboxylic esters into the components by crystallization of diastereomeric salts, which comprises preparing the salts of the racemic esters with optionally active N-acylated R- or S-aminocarboxylic acids which contain a phenyl nucleus, recrystallizing them from an organic solvent, decomposing the precipitated, optically homogeneous diastereomeric salts in a manner known per se, and isolating the enantiomers and, where appropriate, converting the latter into the free acids by hydrolysis in a manner known per se. The invention also relates to optically pure compounds of the formula

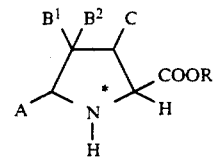

and to diastereomeric salts of these compounds, in which two of the radicals A, $B^1$, $B^2$ and C form a carbon chain and the other denote hydrogen, and R is an esterifying group.

5 Claims, No Drawings

OTHER PUBLICATIONS

L. W. Haynes, Enamines, A. G. Cook, ed., Marcel Decker, Inc.: 1969, pp. 68–79, 261–269, 413.
Fieser & Fieser, Reagents For Organic Synthesis, vol. 1, pp. 644–651 (1967).
Boehme et al., Iminium Salts in Organic Chemistry, Part I (E. C. Taylor, ed.), Wiley & Sons: New York, 1976, p. 143.
S. Dayagi et al., The Chemistry Of Functional Groups. The Chemistry Of The Carbon-Nitrogen Double Bond, S. Patai, ed., Wiley & Sons: New York, 1970, p. 119.
W. Greenlee et al., J. Med. Chem., 28, 434–442 (1985).
K. Ogawa et al., J. Chem. Soc., Perkin Trans. I, 3031–3035 (1982).
R. Bacon and D. Stewart, J. Chem. Soc. (C), 1384–1387 (1966).
R. Bacon et al., J. Chem. Soc. (C), 1388–1389 (1966).
Patchett et al., Nature, 288, 280–283 (1980).
Booth et al., Chemistry and Industry, 466–467 (1956).
Booth et al., J. Chem. Soc., Part I, 1050–1054 (1959).
Murakoshi et al., Chemical Abstracts, 61, 9465(e)(1964).
Cushman et al., Fed. Proc., 38 (13), 2778–2782 (1979).
Houben–Weyl, Methoden der Organischen Chemie, 7(2b), 1403–1404 (1976).
Katritskaya, Dzh. Lagorskaya Khimia Geterosikl. Soedin., Moskow 1963, pp. 155–158.
Anderson, Jr. et al., J. Org. Chem. 43(1), 54–57 (1978).
Bertho et al., "Synthesen In Der 2-Azabicyclo[0.3.-3]-octan-Reihe", Chemische Berichte, 92(7), 2218–2235 (1959).
Farkas et al., J. Org. Chem., 22, 1261–1263 (1957).
Taylor et al., J. Org. Chem., 38(16), 2817–2821 (1973).
Taylor et al., Heterocycles, 25, 343–345 (1987).
English language translation of Mitzlaff et al., Liebig's Ann. Chem., 1713–1733 (1978).
Chem. Berichte 86: 1524–1528 (1953).
Quarterly Reviews 25: 323–341 (1971).
Chem. Abst. 49/1955/3009c.

PROCESS FOR THE RESOLUTION OF RACEMATES OF OPTICALLY ACTIVE BICYCLIC IMINO-α-CARBOXYLIC ESTERS

This application is a continuation of application Ser. No. 07/300,908 filed Jan. 24, 1989, which is a divisional of application Ser. No. 07/023,277 filed Mar. 9, 1987, which is a divisional of Ser. No. 07/575,401 filed Jan. 30, 1984, all abandoned.

The resolution of racemates of aminoacids via crystallization of diastereomeric salts is a widely used process (Review: Boyle, Quart. Rev. 25 (1971) 323). Usually, N-acylated aminoacids are employed, the salts with alkaloid bases are crystallized, and the homogeneous diastereomeric salts are decomposed by, for example, extraction of the N-acyl-aminoacids from the acidified solution (J. Amer. Chem. Soc. 71 (1949) 2541, 3251). It is also possible to carry out the converse process and to crystallize aminoacid esters or amides with optically active acids (Chem. Ber. 86 (1953) 1524).

Optically active compounds, such as 10-camphorsulfonic acid, abietic acid or tartaric acid or their O-derivatives, for example, are used for this purpose. This procedure is particularly appropriate when the intention is to employ optically active aminoacid esters as starting compounds for further syntheses. In this case, it is not advantageous initially to prepare a N-acyl compound and then undertake resolution of the racemate via salt formation with optically active bases, split off the acyl radical and then esterify the free aminoacid.

A process suitable for bicyclic imino-α-carboxylic esters has not hitherto been described. It emerged from experimental tests that all customary acids are unsuitable for resolution of the racemates. A process is known, from European Patent A 37,231, for octahydroindole-2-carboxylic acid, using which the N-benzoyl compound of the racemate can be resolved via the salt with optically active α-phenylethylamine. However, for the reasons mentioned, this process is uneconomical when the esters are required as intermediates for further syntheses.

It has now been found, surprisingly, that N-acyl derivatives of optically active R- or S-aminoacids which contain a phenyl nucleus, such as, for example, S-phenylalnine, tyrosine or tyrosine O-derivatives are suitable as chiral partners for bicyclic imino-α-carboxylic esters. This is because the (S,S)- or (R,R)-salts usually precipitate spontaneously from suitable solvents, while (S,R)- and (R,S)-salts remain in solution. It is possible, in just a single step, to achieve a greater than 95 percent enrichment, and a single recrystallization leads to the optically homogeneous salts in high yield, and these are decomposed in a known manner.

Thus the invention relates to a process for resolving racemic mixtures of bicyclic imino-α-carboxylic esters into the components of the formulae Ia and Ib

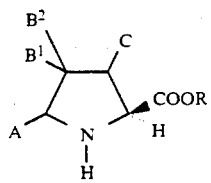
(Ia)

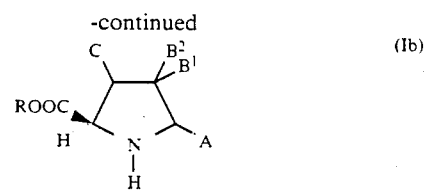
(Ib)

in which
R represents an aliphatic radical having 1 to 6 carbon atoms, an alicyclic radical having 4 to 10 carbon atoms, an aromatic radical having 6 to 12 carbon atoms or an araliphatic radical having 7 to 15 carbon atoms,
a)
   A and $B^1$ denote hydrogen, and
   $B^2$ and C together form a chain of the formula $-[CH_2]_n-$, with n being 3, 4, 5 or 6, or a chain of the formula $-[CH_2]_p-CH=CH-[CH_2]_q-$, with (p+q) being 1, 2, 3 or 4,
b)
   C and $B^2$ denote hydrogen, and
   A and $B^1$ together form a chain of the formula $-[CH_2]_n-$, with n being 3, 4, 5 or 6, or a chain of the formula $-[CH_2]_p-CH=CH-[CH_2]_q-$, with (p+q) being 1, 2, 3 or 4, or
c)
   A and C denote hydrogen, and
   $B^1$ and $B^2$ together form a chain of the formula $-[CH_2]_m-$, with m being 4, 5, 6 or 7,
by crystallization of diastereomeric salts, which process comprises preparing the salts of the racemic esters with optically active N-acylated R- or S-aminocarboxylic acids which contain a phenyl nucleus, recrystallizing them from an aprotic organic solvent or an alcohol having up to 6 carbon atoms, decomposing the precipitated, optically homogeneous diastereomeric salts in a manner known per se, and isolating the enantiomers of the formulae Ia and Ib and, where appropriate, converting the latter into the free acids by hydrolysis or hydrogenolysis in a manner known per se.

Resolution of racemates of compounds of the formula Ia and Ib in which
a)
   A and $B^1$ denote hydrogen, and
   $B^2$ and C together form a chain of the formula $-[CH_2]_n-$, with n being 3, 4, 5 or 6, or a chain of the formula $-[CH_2]_p-CH=CH-[CH_2]_q-$ with (p+q) being 1, 2, 3 or 4, or
b)
   C and $B^2$ denote hydrogen, and
   A and $B^1$ together form one of the chains defined above under a)
is preferred.

A particularly preferred variant of the process comprises precipitating, preferably as crystals, the salts of racemic bicyclic esters of the formulae Ia and Ib in which the two bridgehead hydrogen atoms have the cis configuration and the COOR group is oriented endo with respect to the bicyclic ring system.

Particularly suitable imino-α-carboxylic esters are esters with aliphatic, alicyclic or araliphatic alcohols, which can be cleaved by hydrogenolysis or hydrolysis, as are described in, for example, Houben-Weyl, Methoden der organischen Chemie (Methods of Organic Chemistry), Volume XV/1, Stuttgart 1974, on pages 314-427, or "Peptide Synthesis", by Bodanszky et al., 2nd edition (1976), John Wiley & Sons. Esters of the formula Ia+Ib in which R represents alkyl having 1 to 6 carbon atoms, cycloalkyl having 4 to 8 carbon atoms or aralkyl having 7 to 13 carbon atoms, which can optionally be substituted by $NO_2$, are preferred, in particular alkyl esters having up to 4 alkyl carbon atoms and aralkyl esters, such as benzyl, nitrobenzyl or benzhydryl esters.

Examples of suitable N-acylated aminocarboxylic acids containing a phenyl nucleus are derivatives of R- or S-phenylalanine, -C-phenylglycine, -β-phenyl-α-aminobutyric acid, -3,4-dihydroxyphenylalanine, -β-phenylserine and -tyrosine. N-Acyl derivatives of R- or S-phenylalanine, -C-phenylglycine and -tyrosine are preferred.

The N-acyl protective groups which can be used are the customary $NH_2$ protective groups described in, for example, Houben-Weyl, Volume XV/1, pages 46–305 or Bodanszky et al., "Peptide Synthesis", 2nd edition (1976), John Wiley & Sons. Alkanoyl having 1 to 6 carbon atoms, in particular formyl, tert.-butoxycarbonyl, and benzyloxycarbonyl are preferred. Any free OH groups present can, where appropriate, be O-alkylated by alkyl having 1 to 6 carbon atoms, in particular methyl, ethyl or tert.-butyl, by benzyl or by other OH protective groups customary in peptide chemistry (cf. for example Houben-Weyl, Volume XV/1 or Bodanszky et al., "Peptide Synthesis", 2nd edition (1976), John Wiley & Sons).

Suitable and preferred solvents are aprotic organic solvents, such as, for example, esters, ethyl acetate, cyclohexane and tetrahydrofuran, but it is also possible to use alcohols having up to 6 carbon atoms.

Octahydroindole-2-carboxylic acid is known from U.S. Pat. No. 4,350,704. German Patent Application P 32 26 768.1 relates to 2-azabicyclo[3.3.0]octane-3-carboxylic acid, and German Patent Application P 32 10 496.0 relates to 2,3,3a,4,5,7a-hexahydro[1H]indole-2-carboxylic acid. German Patent Application P 32 11 676.4 relates to octahydroisoindole-1-carboxylic acid and 3-azabicyclo[3.3.0]octane-4-carboxylic acid.

Racemic bicyclic cis, endo-imino-α-carboxylic acids of the formulae Ia+Ib, in which C and $B^2$ denote hydrogen, and A and $B^1$ together denote the abovementioned chain, can be prepared from, for example, enamines of a cycloalkanone and N-acylated β-halogeno-α-aminocarboxylic esters of the formula IV, in which X' represents a nucleofugic group, preferably chlorine or bromine, Y' represents alkanoyl having 1 to 5 carbon atoms, aroyl having 7 to 9 carbon atoms or other protective groups which are customary in peptide chemistry and which can be split off with acid, and $R^4$ represents alkyl having 1 to 5 carbon atoms or aralkyl having 7 to 9 carbon atoms,

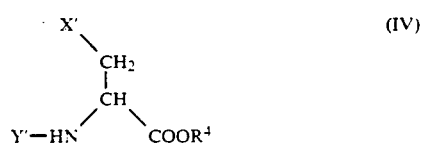
(IV)

or with acrylic esters of the formula V, in which Y' and $R^4$ have the abovementioned meaning,

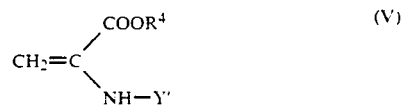
(V)

by reacting the latter to give compounds of the formula VI in which A, $B^1$, $R^4$ and Y' have the abovementioned meaning,

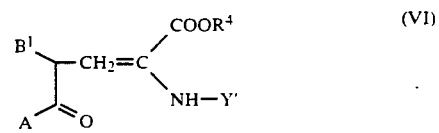
(VI)

cyclizing the latter using strong acids, with cleavage of the acrylamide and ester, to give compounds of the formula VIIa or b,

(VIIa)

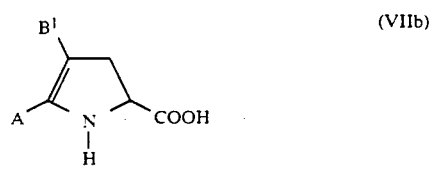
(VIIb)

converting the latter, by catalytic hydrogenation in the presence of transition metal catalysts or by reduction with borane-amine complexes or complex borohydrides in lower alcohols, into compounds of the formulae Ia and Ib in which R represents hydrogen, and esterifying the latter to give compounds of the formulae Ia and Ib in which R has the meaning defined above.

Racemic bicyclic imino-α-carboxylic acids of the formulae Ia and Ib, in which A and $B^1$ denote hydrogen and $B^2$ and C together denote the chain mentioned, can be prepared from, for example, compounds of the formula VIII

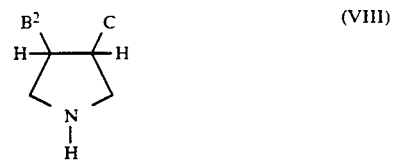
(VIII)

in which the bridgehead hydrogen atoms are oriented cis or trans with respect to one another, and $B^2$ and C have the abovementioned meaning.

Compounds of the formula VIII with n=1 are known from R. Griot, Helv. Chim. Acta 42, 67 (1959), and those with n=2 are known from C. M. Rice et al., J. Org. Chem. 21, 1687 (1955).

These compounds of the formula VIII are acylated in a known manner, an aliphatic or aromatic acyl radical, preferably an acetyl or benzoyl radical, being bonded to the nitrogen atom, and the resulting N-acylated compounds are subjected to anodic oxidation (in analogy to Liebigs Ann. Chem. 1978, page 1719) in an aliphatic alcohol, preferably an alcohol having 1 to 4 carbon atoms, in particular methanol, in the presence of a conducting salt, preferably at temperatures in the range from 0° to +40° C., with the formation of a compound of the formula IX in which B² and C have the abovementioned meaning and R⁵=C₁-C₄-alkyl.

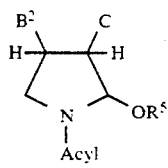
(IX)

The resulting compound of the general formula IX is reacted with trimethylsilyl cyanide by the method of Tetrahedron Letters 1981, page 141, in a hydrocarbon or halogenated hydrocarbon, in ether or in THF, at temperatures in the range from −60° C. to +20° C., preferably −40° C. to ±0° C., in the presence of a Lewis acid, such as, for example, ZnCl₂, SnCl₂, SnCl₄, TiCl₄ or BF₃-etherate, preferably BF₃-etherate, and the resulting compound of the formula X

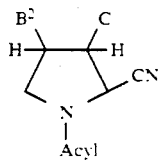
(X)

in which the bridgehead hydrogen atoms are cis or trans with respect to one another, the CN group being located cis with respect to the bridgehead hydrogen atom on carbon atom (4+n), and in which n, B² and C have the abovementioned meanings, is, after purification and resolution of the mixture of diastereomers by recrystallization or column chromatography, hydrolyzed in a known manner by the action of acids or bases to give a compound of the formulae Ia and Ib, with R=hydrogen, and the latter is esterified. HCl or HBr, in particular, is used as the acid for the acid hydrolysis of the nitrile group. In this instance and in those which follow, the esterification is carried out by the procedures customary in aminoacid chemistry.

The invention also relates to optically homogeneous compounds of the formula Ia or Ib in which the two bridgehead hydrogen atoms have the cis configuration, the COOR group is oriented endo with respect to the bicyclic ring system, the carbon atom α to the COOR group has the R or S configuration, R represents alkyl having 1 to 6 carbon atoms, cycloalkyl having 4 to 8 carbon atoms or aralkyl having 7 to 13 carbon atoms, which can optionally be substituted by NO₂, and A, B¹, B² and C are defined as above, and to those compounds of the formulae Ia or Ib in which R denotes hydrogen and a)
A and B¹ denote hydrogen, and
B² and C together form a chain of the formula —[CH₂]ₙ—, with n being 3, 4, 5 or 6, or a chain of the formula —[CH₂]ₚ—CH=CH—[CH₂]q—, with (p+q) being 1, 2, 3 or 4, or b)
C and B² denote hydrogen, and
A and B¹ together form one of the chains defined above a), with n being 3, 5 or 6 and (p+q) being 1, 2, 3 or 4, and their salts.

The invention also relates to diastereomeric salts of a bicyclic cis, endo-imino-α-carboxylic ester of the formula Ia or Ib, in which A, B¹, B², C and R have the meanings defined above as being preferred, and an optically active N-acylated R- or S-aminocarboxylic acid which contains a phenyl nucleus and which is protected as defined above.

The invention also relates to the use of the optically pure compounds of the formula Ia or Ib in a process for the preparation of optically pure compounds of the general formulae IIa or IIb

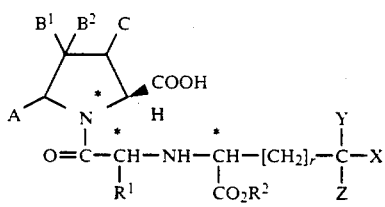
(IIa)

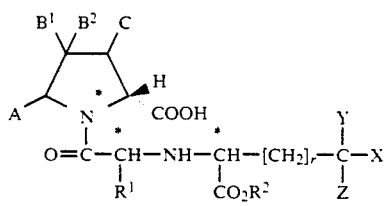
(IIb)

in which it is possible for the carbon atoms labeled with an asterisk (*) each, independently of one another, to have the R- or the S-configuration, a)
A and B¹ denote hydrogen, and
B² and C together form a chain of the formula —[CH₂]ₙ—, n being 3, 4, 5 or 6, or a chain of the formula —[CH₂]ₚ—CH=CH—[CH₂]q—, (p+q) being 1, 2, 3 or 4, b)
C and B² denote hydrogen, and
A and B¹ together form a chain of the formula —[CH₂]ₙ—, with n being 3, 4, 5 or 6, or a chain of the formula —[CH₂]ₚ—CH=CH—[CH₂]q—, with (p+q) being 1, 2, 3 or 4, or c)
A and C denote hydrogen, and
B¹ and B² together form a chain of the formula —[CH₂]ₘ—, with m being 4, 5, 6 or 7, r denotes 0 or 1,
R¹ denotes hydrogen, an optionally substituted aliphatic radical having 1 to 6 carbon atoms, an optionally substituted alicyclic radical having 3 to 9 carbon atoms, an optionally substituted alicyclic-aliphatic radical having 4 to 11 carbon atoms, an optionally substituted aromatic radical having 6 to 12 carbon atoms, which can also be partially hydrogenated, an optionally substituted araliphatic radical having 7 to 15 carbon atoms, an optionally substituted aroylaliphatic radical having 8 to 13 carbon atoms, an optionally substituted monocyclic or bicyclic heterocyclic radical having 5 to 7 or 8 to 10 ring atoms respectively, 1 or 2 of these ring atoms being sulfur or oxygen atoms and/or 1 to 4 of these ring atoms being nitrogen atoms, or a side chain of a naturally occurring aminoacid which is optionally protected,
R² denotes hydrogen, an optionally substituted aliphatic radical having 1 to 6 carbon atoms, or an optionally substituted araliphatic radical having 7 to 15 carbon atoms, Y denotes hydrogen or hydroxyl, Z denotes hydrogen, or Y and Z together denote oxygen, and X denotes an aliphatic radical having 1 to 6 carbon atoms, an alicyclic radical having 5 to 9 carbon atoms, an optionally substituted aromatic radical having 6 to 12 carbon atoms, or indolyl, which process comprises reacting, in the presence of a condensing agent or, where appropriate, as an active ester, optically pure compounds of the formulae Ia or Ib, in which A, $B^1$, $B^2$ and C have the abovementioned meanings, and R represents an optionally substituted aliphatic radical having 1 to 6 carbon atoms, an optionally substituted alicyclic radical having 4 to 10 carbon atoms, an optionally substituted aromatic radical having 6 to 12 carbon atoms or an optionally substituted araliphatic radical having 7 to 15 carbon atoms, with optically pure compounds of the formula III

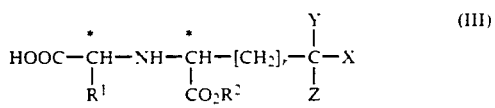

(III)

in which the two carbon atoms labeled with an asterisk (*) have the (S,R), (R,S), (R,R) or, preferably, (S,S) configuration, and R, $R^1$, $R^2$, X, Y and Z have the abovementioned meanings, splitting off the radical R by hydrogenolysis or hydrolysis, and, where appropriate, converting the optically pure compounds of the formulae IIa or IIb into physiologically tolerated salts.

A preferred embodiment of the process according to the invention comprises preparing compounds of the formulae IIa or IIb, in which r denotes 0 or 1, R denotes hydrogen, ($C_1$ to $C_6$)-alkyl or aralkyl having 7 to 9 carbon atoms, $R^1$ denotes hydrogen or ($C_1$ to $C_6$)-alkyl, which can optionally be substituted by amino, ($C_1$ to $C_6$)-acylamino or benzoylamino, ($C_2$ to $C_6$)-alkenyl, ($C_5$ to $C_9$)-cycloalkyl, ($C_5$ to $C_9$)-cycloalkenyl, ($C_5$ to $C_7$)-cycloalkyl-($C_1$ to $C_4$)-alkyl, aryl or partially hydrogenated aryl having 6 to 12 carbon atoms, each of which can be substituted by ($C_1$ to $C_4$)-alkyl, ($C_1$ or $C_2$)-alkoxy or halogen, ($C_6$ to $C_{12}$)-aryl-($C_1$–$C_4$)-alkyl or ($C_7$–$C_{13}$)-aroyl-($C_1$–$C_2$)-alkyl, both of which can be substituted in the aryl radical as defined above, a monocyclic or bicyclic heterocyclic radical having 5 to 7 or 8 to 10 ring atoms respectively, 1 or 2 of these ring atoms being sulfur or oxygen atoms and/or 1 to 4 of these ring atoms being nitrogen atoms, or an optionally protected side chain of a naturally occurring aminoacid, $R^2$ denotes hydrogen, ($C_1$ to $C_6$)-alkyl, ($C_2$ to $C_6$)-alkenyl or ($C_6$ to $C_{12}$)-aryl-($C_1$ to $C_4$)-alkyl, Y denotes hydrogen or hydroxyl, Z denotes hydrogen, or Y and Z together denote oxygen, and X denotes ($C_1$ to $C_6$)-alkyl, ($C_2$ to $C_6$)-alkenyl, ($C_5$ to $C_9$)-cycloalkyl, ($C_6$ to $C_{12}$)-aryl, which can be monosubstituted, disubstituted or trisubstituted by ($C_1$ to $C_4$)-alkyl, ($C_1$ to $C_4$)-alkoxy, hydroxyl, halogen, nitro, amino, ($C_1$ to $C_4$)-alkylamino, di-($C_1$ to $C_4$)-alkylamino and/or methylenedioxy, or 3-indolyl.

The preparation of the S,S,S,-compounds of the formula IIa is preferred.

In this context as in the following, aryl is to be understood preferably to include optionally substituted phenyl or naphthyl. Alkyl can be straight-chain or branched.

Examples of a monocyclic or bicyclic heterocyclic radical having 5 to 7 or 8 to 10 ring atoms respectively, in which the ring atoms have the abovementioned meanings, include thienyl, benzo[b]thienyl, furyl, pyranyl, benzofuryl, pyrrolyl, imidazolyl, pyrazolyl, pyridyl, pyrimidinyl, pyridazinyl, indazolyl, isoindolyl, indolyl, purinyl, quinolizinyl, isoquinolinyl, phthalazinyl, naphthyridinyl, quinoxalinyl, quinazolyl, cinnolinyl, pteridinyl, oxazolyl, isoxazolyl, thiazolyl or isothiazolyl. It is also possible for these radicals to be partially or completely hydrogenated.

Where $R^1$ represents a side chain of a protected naturally occurring α-aminoacid, such as, for example, protected or optionally substituted Ser, Thr, Asp, Asn, Glu, Gln, Arg, Lys, Hyl, Cys, Orn, Cit, Tyr, Trp, His or Hyp, the preferred protective groups are those groups customary in peptide chemistry (cf. Houben-Weyl, Vol.XV/1 and XV/2). In the case where $R^1$ denotes a protected side chain of a lysine, the known amino protective groups, but in particular ($C_1$–$C_6$)-alkanoyl, are preferred. Preferred O-protective groups for tyrosine are methyl or ethyl.

In the procedures hitherto known for preparing mixtures of stereoisomers of compounds of the formulae IIa or IIb, which started from mixtures of stereoisomers, it was necessary to use elaborate separating procedures to separate the reaction mixture in order to obtain the desired optically pure stereoisomers of the formula IIa or IIb. By reacting the optically homogeneous imino-α-carboxylic esters of the formulae Ia or Ib according to the invention with optically homogeneous compounds of the formula III, specific synthesis of optically homogeneous compounds of the formula IIa or IIb has become possible. The desired compounds of the formulae IIa or IIb are obtained in high yields without using elaborate separating techniques.

Compounds of the formula III are described in the abovementioned documents or are known from European Patent A 46,953. The reaction of a compound of the formula III with tert.-butyl 1-(2α,3αβ,7αβ)-octahydro-[1H]-indole-2-carboxylate followed by elimination of a tert.-butylester, whereupon a corresponding octahydroindole derivative of the formula IIb results, is known from European Patent A 37,231.

However, it has been necessary to restrict this reaction to reaction of a compound of the formula Ia or Ib with C and $B^2$ each being H and A+$B^1$ being $(CH_2)_4$, and it has hitherto only been possible to prepare this in a complicated manner via the N-benzoyl compound, crystallization of the diastereomeric salts with S-α-phenylethylamine, liberation of the N-benzoyl compound, elimination of the benzoyl group and esterification.

It has not hitherto been possible to transfer this reaction sequence to the intermediates of the formula Ia and Ib according to the invention. Nor has it been possible to resolve racemic mixtures of compounds of the formula IIa and IIb by separating conventional diastereomeric salts with optically active carboxylic or sulfonic acids. The compounds of the formula Ia and Ib have been made accessible for subsequent reactions for the first time by the procedure described above.

The process according to the invention is particularly cost-effective, since compounds of the formula III can be prepared directly in an optically pure form by straightforward routes from German Patent Application P 32 26 768.1. However, in this reference, it was still necessary for these intermediates to be reacted with a racemic aminoacid and to be converted into an optically pure compound of the general formulae IIa and IIb by an additional purification step.

The process according to the invention, which is preferably carried out with S,S compounds of the formula III, thus represents by far the most cost-effective process for the preparation of the compounds covered since, in all the other known procedures, great losses have to be accepted due to the chromatography or crystallization of mixtures of stereoisomers, some of which are complex.

The condensation step is carried out by one of the conventional processes of peptide synthesis which involve little racemization, such as are described in, for example, Houben-Weyl, Volume XV, or in "The Peptides—Analysis, Synthesis, Biology, Vol.1 Major Methods of Peptide Bond Formation, Part A", Gross, Meierhofer, Academic Press N.Y. (1979). The DCC/HOBt method of Chem. Ber. 103 (1979), pages 788-798, is particularly advantageous. In this context, it should be taken into account that reactive functional groups in the radical $R^1$ must be temporarily protected by the known methods of peptide chemistry (for example Houben-Weyl, Volume XV, or Bodanszky et al. in "Peptide Synthesis", 2nd edition (1976), John Wiley & Sons).

The optically homogeneous compounds of the formula IIa or IIb are obtained, after eliminating R and, where appropriate, $R^2$, in high yield in a manner known per se without using elaborate separating techniques.

The compounds of the formula IIa and IIb and their salts have long-lasting and powerful hypotensive activity. They are potent inhibitors of angiotensin converting enzyme (ACE) and can be employed to control high blood pressure of a variety of etiologies. ACE inhibitors of this type are known from, for example, U.S. Pat. No. 4,344,949, European Patent A 49,658, European Patent A 46,953, European Patent A 50,800 and European Patent A 79,022.

It is also possible to combine them with other compounds having hypotensive, vasodilator or diuretic activity. Typical representatives of these classes of active compounds are described in, for example, Erhardt-Ruschig, Arzneimittel (Drugs), 2nd edition, Weinhein, 1972. They can be administered intravenously, subcutaneously or orally.

The dosage on oral administration is generally 1-500 mg, preferably 1-100 mg, per single dose for an adult patient of normal weight. It is also possible to increase this in severe cases, since no toxic properties have hitherto been observed. It is also possible to reduce the dose and this is particularly appropriate when diuretics are administered concurrently.

The compounds according to the invention can be administered orally or parenterally in appropriate pharmaceutical formulations. For a form for oral use, the active compounds are mixed with the additives customary for this purpose, such as vehicles, stabilizers or inert diluents, and converted by customary methods into suitable forms for administration, such as tablets, coated tablets, hard gelatin capsules, aqueous, alcohol or oily suspensions or aqueous, alcohol or oily solutions. Examples of suitable inert vehicles which can be used are gum arabic, magnesium carbonate, potassium phosphate, lactose, glucose or starch, in particular corn starch. This can entail formulation either as dry or as moist granules. Examples of suitable oily vehicles or solvents are vegetable or animal oils, such as sunflower oil or fish liver oil.

For subcutaneous or intravenous administration, the active compounds or their physiologically tolerated salts are converted into a solution, suspension or emulsion, where appropriate with the substances customary for this purpose, such as solubilizers, emulsifiers or other auxiliaries. Examples of suitable solvents for the new active compounds and the corresponding physiologically tolerated salts are: water, physiological saline or alcohols, for example ethanol, propanediol or glycerol, but also sugar solutions, such as glucose or mannitol solutions, or even a mixture of the various solvents or solutions mentioned.

The Examples which follow illustrate the process, but there is no intention to restrict the invention to these specific Examples.

EXAMPLE 1

Benzyl (1S, 3S, 5S)-2-azabicyclo[3.3.0]octane-3-carboxylate hydrochloride (abbreviated to (S)-Aoc-OBzl-HCl)

(A) Methyl 2-acetylamino-3-(2-oxocyclopentyl)propionate 269 g of methyl 3-chloro-2-acetylaminopropionate and 257 g of cyclopentenopyrrolidine in 1.5 liters of DMF are kept at room temperature for 24 hours. The mixture is evaporated in vacuo, and the residue is taken up in a little water, the pH is adjusted to 2 with concentrated hydrochloric acid and the solution is extracted twice with 4 liters of ethyl acetate each time. A pale yellow oil remains on evaporating the organic phase.

Yield: 290 g.

$^1$H-NMR:2.02 (s,3H); 3.74 (s,3H); 4.4-4.8 (m,1H), (CDCl$_3$)

| Analysis: | C | H | N |
|---|---|---|---|
| calculated | 58.1 | 7.54 | 6.16 |
| found | 58.5 | 7.2 | 6.5 |

(B) cis,endo-2-Azabicyclo[3.3.0]octane-3-carboxylic acid hydrochloride 270 g of the acetylamino derivative prepared under (A) in 1.5 liters of 2N hydrochloric acid are boiled under reflux for 45 minutes. The mixture is evaporated in vacuo, and the residue is taken up in glacial acetic acid, 5 g of Pt/C (10% Pt) are added and hydrogenation is carried under 5 bar. After filtration, the filtrate is evaporated and the residue is crystallized from chloroform/diisopropyl ether.

Melting point: 205°-209° C.,
Yield: 150 g (C) Racemic Aoc-OBzl.HCl 1.2 liters (11.5 mol) of benzyl alcohol are cooled to −10° C. 126 ml (1.73 mol) of thionyl chloride are added dropwise, with cooling and stirring, and then 126.5 g (0.66 mole) of crude Aoc.HCl are added at −10° C., with stirring, and the mixture is then stirred at this temperature for 30 minutes. The temperature is then allowed to rise slowly to 20°-25° C. with stirring, the product dissolving within 5 hours. After standing overnight, the brown solution is run into 4.0 liters of diisopropyl ether with stirring. After 1 hour, the precipitated crystals are filtered off, washed with diisopropyl ether and dried in vacuo. A further precipitate separates out of the combined diisopropyl ether solutions overnight.

Yield: 168.5 g (90.6%)

(D) (S)-Aoc-OBzl.Z-Phe-OH 166.0 g (0.589 mol) of racemic Aoc-OBzl.HCl are suspended in 500 ml of methylene chloride and thoroughly shaken with 25 g (0.625 mol) of NaOH in 250 ml of water. A solution is produced. After a short time, the initially formed emulsion has separated. The methylene chloride phase is separated off, washed with 100 ml of 0.1N NaOH and twice with 50 ml of water each time and the combined aqueous phases are extracted twice with 100 ml of methylene chloride each time. The combined methylene chloride phases are dried over sodium sulfate and evaporated under mild conditions with waterpump vacuum. The remaining oil is immediately taken up in 100 ml of ethyl acetate, and a solution of 117.6 g (0.39 mol) of N-benzyloxycarbonyl-S-phenylalanine (Z-Phe-OH) in 200 ml of ethyl acetate is added. The flask is rinsed with 100 ml of ethyl acetate. 1,600 ml of cyclohexane (=4 times the amount by volume) are added, with stirring, to the clear solution at room temperature. After scratching, crystallization starts, and this is completed by standing overnight in a cold room. The crystalline precipitate is filtered off, washed with 250 ml of ethyl acetate/cyclohexane (1+4) and dried.

Yield: 133.6 g of (S)-Aoc-OBzl.Z-Phe-OH (50.9%, corresponding to 102% of theory), melting point 101°-103° C.; $[\alpha]_D^{27}$: −5.3° (c=1, methanol).

After recrystallization from ethyl acetate/cyclohexane (1:1), the following data are found for the Z-Phe-OH salt:

melting point: 103°-104° C., $[\alpha]_D^{27}$: −6.1° (c=1, in methanol).

(E) (S)-Aoc-OBzl.HCl 63.0 g (0.142 mole) of the Z-Phe-OH salt obtained according to (D) are dissolved in 300 ml of methylene chloride and the solution is thoroughly shaken with 6.0 g (0.15 mole) of NaOH in about 150 ml of water. Phase separation takes some time because of a small amount of insolubles. The methylene chloride phase is separated off, washed with 50 ml of 0.1N NaOH and twice with 50 ml of water each time and dried. The solution is evaporated to about 100 ml, diluted with 100 ml of diisopropyl ether and, with stirring, 25 ml of 6N HCl in ether are added. After 1 hour, the mixture is filtered, and the precipitate is washed with diisopropyl ether and dried.

Yield: 32.5 g (81.3%)

Melting point: 185°-186° C.

$[\alpha]_D^{30}$: −42.5° (c=1, water)

Methylene chloride is removed from the basic aqueous phase in vacuo, and it is acidified with concentrated HCl. The precipitated Z-Phe-OH is washed with water and dried.

The R compound and further Z-Phe-OH are obtained from the methylene chloride mother liquor from Example I(D) in the manner described.

TABLE 1

| Example | Iminocarboxylic acid | Ester R | Acid | Solvent | Diastereoisomeric Salts m.p. | $[\alpha]_D^{20}$ (c = 1, MeOH) |
|---|---|---|---|---|---|---|
| 2 | XIII | Methyl | Z—Phe—OH | Diethyl ether | 115–116° C. | +5.8° |
| 3 | XIII | Benzyl | Z—Phe—OH | Ethyl acetate/cyclohexane | 104–105° C. | +6.2° |
| 4 | XIII | Benzyl | Z—Phe—OH | Isopropanol | 103–104° C. | −6.0° |
| 5 | XIII | Benzyl | Z—R—Phe—OH | Ethyl acetate/cyclohexane | 102–104° C. | +4.4° |
| 6 | XIII | Benzyl | Z—Pgl—OH | Ethyl acetate | 128–130° C. | +32.1° |
| 7 | XIII | Benzyl | Z—Tyr—OH | Ethyl acetate/cyclohexane | 125–126° C. | −0.4° |
| 8 | XIII | Benzyl | Z—Tyr(But)-OH | Ethyl acetate/cyclohexane | 104–105° C. | −3.4° |
| 9 | XIII | Benzyl | For—Phe—OH | Isopropanol | 107–109° C. | +1.7° |
| 10 | XIII | Nitrobenzyl | Z—Phe—OH | Ethyl acetate | 122–124° C. | −1.3° |
| 11 | XI | Benzyl | Z—Phe—OH | Ethyl acetate/cyclohexane | 106–107° C. | −13.5° |
| 12 | XII | Methyl | Z—Phe—Oh | Ethyl acetate/cyclohexane | 107–108° C. | +47.1° |

| Example | Acid component | Final product S-Form m.p. | S-Form $[\alpha]_D^{20}$ (c = 1, H$_2$O) | R-Form m.p. | R-Form $[\alpha]_D^{20}$ (c = 1, H$_2$O) |
|---|---|---|---|---|---|
| 2 | TosOH | 191–192° C. | −12.9° | 190–192° C. | +12.6° |
| 3 | HCl | 184–186° C. | −41.2° | 183–185° C. | +42.5° |
| 4 | HCl | 182–185° C. | −39.9° | | |
| 5 | HCl | | | 185–186° C. | +41.9° |
| 6 | HCl | 184–185° C. | −40.9° | | |
| 7 | HCl | 184–185° C. | −41.6° | | |
| 8 | HCl | 181–183° C. | −40.0° | | |
| 9 | HCl | 178–181° C. | −39.1° | | |
| 10 | TosOH | | −29.8° | | |
| 11 | TosOH | 152–153° C. | −36.2° | | |
| 12 | HCl | | +68.4° | | |

The [cis,endo]-imino-α-carboxylic esters in Table 1 are prepared and subjected to racemate resolution in an analogous manner. This Table details their optically active crystallization partners, and the solvents, yields and properties of the salts and the final products in the form of the ester hydrochlorides or ester tosylates.

Explanations of Table 1

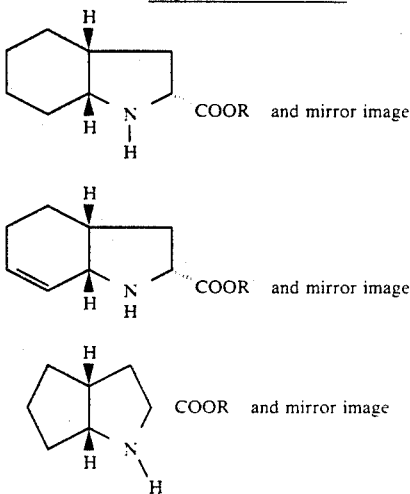

The free iminocarboxylic acids can be prepared from the esters by hydrolysis or hydrogenolysis.

EXAMPLE 13

N-(1S-Carboethoxy-3-phenylpropyl)-S-alanyl-2-cis,endo-azabicyclo[3.3.0]-octane-3S-carboxylic acid (A) Benzyl N-(2S-carboethoxy-3-phenylpropyl)-S-alanyl-cis,endo-2-azabicyclo[3.3.0]octane-3S-carboxylate 14 g of the benzyl ester hydrochloride prepared according to Example 1 E are converted into the free ester by extracting by shaking the alkaline aqueous solution with diethyl ether, and, after distilling out the ether, are reacted with 6.7 g of HOBt, 13.8 g of N-(1S-carboethoxy-3-phenylpropyl)-S-alanine and 10.2 g of dicyclohexylcarbodiimide in 200 ml of dimethylformamide. After stirring at room temperature for 3 hours, the precipitated dicyclohexylurea is filtered off, and the filtrate is evaporated, and the residue is taken up in 1 liter of ethyl acetate and this solution is extracted by shaking with $3 \times 500$ ml of 5 percent $NaHCO_3$ solution. The organic phase is evaporated.

22.4 g (90%) of product are obtained as an oil. $^1$HNMR of the S,S,S-compound, characteristic signals: 1.20 (d,3H), 1.27 (t,2H), 4.17 (q,3H), 5.13 (s,2H), 7.18 (s,5H), 7.32 (s,5H) ($CDCl_3$)

| Analysis: | | C | H | N |
|---|---|---|---|---|
| $C_{30}H_{38}N_2O_5$ | calculated | 71.1 | 7.56 | 5.53 |
| | found | 70.8 | 7.8 | 5.7 |

(B) N-(1S-Carboethoxy-3-phenylpropyl)-S-alanyl-cis,endo-2-azabicyclo[3.3.0]octane-3S-carboxylic acid 8.0 g of the S,S,S-benzyl ester from Example 1 E are dissolved in 100 ml of ethanol, and the benzyl group is removed by hydrogenolysis under atmospheric pressure with the addition of 0.5 g of 10% Pd/C. This reaction can also be carried out under elevated pressure which involves shortening of the reaction time. After the calculated amount of hydrogen has been taken up, the catalyst is filtered off and the filtrate is evaporated in vacuo. The zwitterion crystallizes from ether in a virtually quantitative yield:

melting point: 110°–112° C. (decomposition)

A hydrochloride (decomposition above 120° C.) can be obtained by addition of an equivalent amount of hydrochloric acid.

| Analysis: | | C | H | N |
|---|---|---|---|---|
| $C_{23}H_{32}N_2O_5$ | calculated | 66.3 | 7.7 | 6.73 |
| | found | 66.1 | 7.8 | 6.6 |

The $^1$H NMR and mass spectra which are obtained are consistent with the structure indicated.

$[\alpha]_D = +15.6°$ (c=1, methanol).

EXAMPLE 14

N-(1S-Carboethoxy-2-benzoylethyl)-O-ethyl-S-tyrosyl-cis,endo-2-azabicyclo[3.3.0]octane-3S-carboxylic acid (A) N-(1S-Carboethoxy-3-phenylpropyl)-O-ethyl-S-tyrosine benzyl ester 24 g of ethyl benzoylacrylate in 100 ml of ethanol are reacted with 30 g of O-ethyl-S-tyrosine benzyl ester in the presence of 0.5 ml of triethylamine and, after evaporating the solution and digesting the residue with diethyl ether/petroleum ether (1:1) and drying in vacuo, 42 g of RS,S compound are obtained. Resolution of the diastereomers by chromatography on silica gel using the system ethyl acetate/cyclohexane (1:3).

Yield: 17 g of the S,S compound.

(B) N-(1S-Carboethoxy-3-phenylpropyl)-O-ethyl-S-tyrosine 17 g of the compound obtained according to (A) in 800 ml of acetic acid are hydrogenated with 4 g of Pd/C (10%) under 100 bar and at room temperature. Yield after chromatography on silica gel using the solvent ethyl acetate/cyclohexane (1:3) and drying the residue from evaporation: 12 g of title compound which is virtually homogeneous by thin-layer chromatography.

Melting point 205°–213° C.

Analysis: $C_{23}H_{29}NO_5$ (399.5): calculated: C 69.15, H 7.31, N 3.50. found C 69.5, H 7.4, N 3.3.

(C) N-(1S-Carboethoxy-3-phenylpropyl)-O-ethyl-S-tyrosyl-cis,endo-2-azabicyclo[3.3.0]octane-3S-carboxylic acid In analogy to Example 13 A, 8 g of the free benzyl ester obtained in accordance with Example 1 E and extracted from alkaline solution by shaking with diethyl ether are reacted with 8 g of the compound obtained in accordance with Example 14 B using 4.4 g of dicyclohexylcarbodiimide in the presence of 2.7 g of 1-hydroxybenzotriazole, and 14.3 g of oily benzyl ester are obtained as an intermediate.

The $^1$H NMR and mass spectra are consistent with the structure indicated.

The benzyl ester in 50 ml of ethanol is catalytically hydrogenated on Pd/C under atmospheric pressure.

After filtering off the catalyst and distilling off the solvent, there remains a solid residue which is digested with diethyl ether/petroleum ether and is dried.

Yield: 11.2 g

EXAMPLE 15

N-(1S-Carboethoxy-3-phenylpropyl)-O-methyl-S-tyrosyl-cis,endo-2-azabicyclo[3.3.0]octane-3S-carboxylic acid The procedure is carried out as described in Example 14, but in the stage analogous to (A) O-methyl-S-tyrosine benzyl ester is used and the title compound is obtained, the $^1$H NMR spectrum of which is consistent with the structure indicated.

$^1$H NMR (CDCl$_3$): 1.2–3.0 (m,15H); 1.27 (t,3H); 1.4 (t,3H); 3.0–4.3 (m,4H); 3.8–4.2 (m,4H); 6.5–7.1 (2d,4H); 7.3 (s,5H)

EXAMPLE 16

N-(1S-Carboethoxy-3-phenylpropyl)-S-alanyl-2-azaspiro[4.5]decane-3S-carboxylic acid

(A) 1-(Diethoxyethyl)cyclohexanecarbonitrile 51.7 ml (0.5 mol) of anhydrous diethylamine are added dropwise, under protective gas at −10° C., to 312.5 ml (0.5 mol) of a 15% strength solution of n-butyllithium in hexane. The mixture is stirred for 20 minutes and then cooled to −70° C. 54.6 g of cyclohexanecarbonitrile are added dropwise over the course of 30 minutes and, after a further 30 minutes, 98.5 g of bromoacetaldehyde diethyl acetal are added within 1 hour and the mixture is left at low temperature for 24 hours. It is then warmed to room temperature, 100 g of ice are added, and the mixture is extracted twice with 500 ml of ethyl acetate, and the organic phase is dried over sodium sulfate, evaporated in vacuo and the residue is subjected to vacuum distillation.

Yield: 90 g (about 80% of theory), boiling point 78°–79° C. at 8 torr (10.7 mbar).

(B) 1-Aminomethyl-1-(diethyloxyethyl)cyclohexane 90 g of diethyloxycyclohexanecarbonitrile are dissolved in 1 liter of ethanol, and 60 g of sodium are added. After the metal has dissolved, 100 ml of water are added and the solvent is largely removed in vacuo. 300 ml of water are added to the residue and the mixture is extracted 3× with 200 ml of ether. The ethereal phase is dried over sodium sulfate, evaporated and distilled in vacuo.

Yield: 83 g (about 90% of theory), boiling point 69°–72° at 8 torr (10.7 mbar)

(c) 2-Azaspiro[4.5]decane-3-carbonitrile 80.2 g of aminomethyldiethyloxycyclohexane are stirred in a mixture of 300 ml of ethanol and 300 ml of 1N hydrochloric acid under a protective gas (N$_2$ or Ar) for about 1 hour.

After the starting product has been completely cleaved, the mixture is cooled to 0° C. and the solution is rapidly adjusted to pH 5 by adding 2N sodium hydroxide solution. 300 ml of glacial acetic acid are immediately added (pH about 3), and the mixture is cooled to −10° C. and 17.5 g of sodium cyanide are added. The reaction vessel is closed and left at room temperature for about 5 hours. Completion of reaction is checked using thin-layer chromatography (system ethyl acetate/petroleum ether 2:1) (Schiff's base R$_f$=0.6–0.7; aminoacid nitrile R$_f$=0.28) and the reaction solution is evaporated to dryness. The crude aminoacid nitrile is immediately processed further in accordance with Example 16 D or E.

(D) 2-Azaspiro[4.5]decane-3-carboxylic acid 250 ml of 4N hydrochloric acid are added to one half of the aminoacid nitrile obtained in Example 16 C, and the mixture is heated under reflux for 4 hours. Traces of escaping hydrocyanic acid are made harmless in a suitable manner (freezing out, absorption in basic iron(II) salt solution). The solution is neutralized, evaporated to dryness and extracted several times with n-butanol. The residue from evaporation of the organic phase is a) crystallized from chloroform/diisopropyl ether to obtain the hydrochloride and, if necessary, again precipitated from a mixture with ethanol or b) purified in aqueous solution by stirring with an ion exchanger, for example IR 45 (OH form) (Amberlite ®) and, after removing the water, the zwitterion is crystallized from ethanol/ether.

Yield from a): 31–32 g (82%)

Melting point 205° C. (decomposition), hydrochloride

(E) Benzyl 2-azaspiro[4.5]decane-3-carboxylate hydrochloride

Half of the aminoacid nitrile obtained in accordance with Example 16 C is taken up in 70 ml of benzyl alcohol. A slow stream of HCl gas is passed through the solution at room temperature for 5 minutes, then it is maintained at room temperature for 2–3 hours, evaporated to a small volume in vacuo, and aqueous sodium bicarbonate solution is added until the pH is 8.5 and the benzyl ester is extracted into ethyl acetate. The organic phase is dried, an equivalent amount of ethereal hydrochloric acid is added and the mixture is evaporated. The residue crystallizes from diisopropyl ether and can be recrystallized from methylene chloride/diisopropyl ether.

Yield: 43 g (about 80%)

Melting point 145° C. (decomposition)

(F) Benzyl 2-azaspiro[4.5]decane-3S-carboxylate hydrochloride

The racemic hydrochloride obtained in accordance with Example 16 E is subjected to racemate resolution in analogy to Examples 1 D and E.

(G) Benzyl N-(1S-carboethoxy-3-phenylpropyl)-S-alanyl-2-azaspiro[4.5]nonane-3S-carboxylate 15.6 g of benzyl 2-azaspiro[4.5]nonane-3S-carboxylate hydrochloride, 6.7 g of 1-hydroxybenzotriazole and 13.8 g of (S,S)-N-(1-carboethoxy-3-phenylpropyl)alanine are dissolved in 200 ml of DMF and reacted overnight with 10.2 g of dicyclohexylcarbodiimide. Addition of tertiary bases, for example 6.4 ml of N-ethylmorpholine, increases the yield only inconsiderably. The precipitated DC-urea is filtered off, the filtrate is evaporated in vacuo, the residue is taken up in ethyl acetate, and the solution is extracted by shaking with aqueous sodium bicarbonate solution, and the organic phase is dried over solid sodium sulfate and again evaporated. The $^1$H NMR spectra (in CDCl$_3$) confirm the structure.

(H)

N-(1S-Carboethoxy-3-phenylpropyl)-S-alanyl-2-azaspiro[4.5]nonane-3S-carboxylic acid The benzyl ester obtained in Example 16 G is taken up in 200 ml of methanol and the benzyl group is removed by hydrogenolysis with 1 g of Pd/C (10% Pd). After uptake of hydrogen is complete, the mixture is filtered and the filtrate is evaporated in vacuo. A solid, hygroscopic foam of the zwitterionic dipeptide derivative can be obtained in vacuo with the addition of pentane.

$[\alpha]_D^{21} = 38.3°$ (c=1, methanol)

EXAMPLE 17

N-(1S-Carboethoxy-3-phenylpropyl)-S-alanyl-cis,endo-2,3,3a,4,5,7a-hexahydro[1H]indole-2S-carboxylic acid (a) Methyl cis-2,3,3a,4,5,7a-hexahydro[1H]indole-2S-carboxylate hydrochloride Racemic methyl cis-2,3,3a,4,5,7a-hexahydro[1H]indole-2-carboxylate hydrochloride (obtainable in analogy to the procedure described in German Patent Application P 32 10 496.0) is subjected to racemate resolution in analogy to Examples 1 D and E.

$[\alpha]_D = +68.4°$ (c=1, H$_2$O)

(B)

N-(1S-Carboethoxy-3-phenylpropyl)-S-alanyl-cis,endo-2,3,3a,4,5,7a-hexahydro[1H]indole-2S-carboxylic acid hydrochloride The title compound is obtained by a procedure analogous to that described in Examples 13 A and B.

$^1$H NMR data 0.9-3.0 (m, 17H); 3.4-4.9 (m, 6H); 5.2-6.0 (m, 2H); 7.2 (s, 5H).

We claim:

1. Cis,endo-2-Azabicyclo[3.3.0]octane-3S-carboxylic acid, essentially free of other isomers.

2. A cis,endo-2-azabicyclo[3.3.0]octane-3S-carboxylic ester, essentially free of other isomers, in which the ester group is denoted by —COOR, where R represents alkyl having 1 to 6 carbon atoms, cycloalkyl having 4 to 8 carbon atoms or aralkyl having 7 to 13 carbon atoms which can optically be substituted by NO$_2$.

3. Benzyl cis,endo-2-azabicyclo[3.3.0]octane-3S-carboxylate, essentially free of other isomers.

4. A cis,endo-octahydro[1H]indole-2S-carboxylic ester, essentially free of other isomers, in which the ester group is denoted by —COOR, where R represents alkyl having 1 to 6 carbon atoms, cycloalkyl having 4 to 8 carbon atoms or aralkyl having 7 to 13 carbon atoms which can optionally be substituted by NO$_2$.

5. Benzyl cis,endo-octahydro[1H]indole-2S-carboxylate, essentially free of other isomers.

* * * * *

UNITED STATES PATENT AND TRADEMARK OFFICE
CERTIFICATE OF CORRECTION

PATENT NO. : 5,175,306
DATED : December 29, 1992
INVENTOR(S) : Rolf Geiger et al.

It is certified that error appears in the above-indentified patent and that said Letters Patent is hereby corrected as shown below:

TITLE PAGE, ITEM [30]
Under "Foreign Application Priority Data", insert
--Jan. 31, 1983 Fed. Rep. of Germany.........3303139--.

Signed and Sealed this

Tenth Day of May, 1994

*Attest:*

BRUCE LEHMAN

*Attesting Officer*  Commissioner of Patents and Trademarks